United States Patent [19]
Gokhale et al.

[11] Patent Number: 6,087,136
[45] Date of Patent: Jul. 11, 2000

[54] MICROBIAL PROCESS FOR THE PRODUCTION OF D(-)-N-CARBAMOYLPHENYLGLYCINE

[75] Inventors: Digambar Vitthal Gokhale; Kulbhushan Balwant Bastawde; Shamrao Ganapatrao Patil; Uttam Ramrao Kalkote; Rohini Ramesh Joshi; Ramesh Anna Joshi; Thottapillil Ravindranathan; Vithal Venkatrao Jogdand; Bhaskar Ganapatrao Gaikwad; Sanjay Narayan Nene, all of Pune, India

[73] Assignee: Council of Scientific & Industrial Research, New Delhi, India

[21] Appl. No.: 08/828,610

[22] Filed: Mar. 31, 1997

[51] Int. Cl.[7] .................................................... C12P 13/04
[52] U.S. Cl. ........................ 435/106; 435/108; 435/252.1; 435/253.3
[58] Field of Search .................................... 435/108, 106, 435/252.1, 253.3

[56] References Cited

U.S. PATENT DOCUMENTS 4,094,741  6/1978  Yamada ................................... 435/106
4,111,749  9/1978  Degen ...................................... 435/106

OTHER PUBLICATIONS

Sun, Wanru., Acta Microbiol Sin, (1983) 23 (2), 133–142.

*Primary Examiner*—Irene Marx
*Attorney, Agent, or Firm*—Dinesh Agarwal, P.C.

[57] ABSTRACT

A microbial process for the preparation of D(-)-N-carbamoylphenylglycine from DL-5-phenylhydantoin which comprises culturing the strain pseudomonas sp. having Accession No. NCIM 5070 (ATCC 55940) and deposited in National Collection of Industrial microorganisms (NCIM), National Chemical laboratory (NCL) (India), having hydantoinase activity, in a medium for 16–20 hours, separating the cells by centrifugation, treating the solid cells obtained with DL-5-phenylhydantoin in buffer, at a temperature in the range of about 25–30° C. for a period of about 2–6 hours, acidifying the mixture to obtain solid D(-)-N-carbamoylphenylglycine, and separating the product by filtration.

2 Claims, No Drawings

MICROBIAL PROCESS FOR THE PRODUCTION OF D(–)-N-CARBAMOYLPHENYLGLYCINE

This invention relates to the novel microbial process for the production of D(–)-phenylglycine via D(–)-N-carbamoylphenylglycine from DL-5-phenylhydantoin.

D(–)-α-Amino acids are useful intermediates for the synthesis of peptide drugs and β- lactam antibiotics (semisynthetic penicillins & cephalosporins). Several chemical methods for the production of optically active amino acids from racemic amino acids have been investigated [K. Gerad. Ger. pat. 2,844,202 (1979), CA:91, 123995 (1979); W. Hasting, P. Charles R; Brit. Pat., 1,455,710 (1976), CA:86, 155969 (1977); S. Haruhiko, K. Yuichi Jpn. Kokai 7,695,036 (1976), CA:86, 44028 (1977); J. C. Clark, G. H. Phillips, M. R. Steer and L. Stephenson, J. C. S. Perkin I, 471–474 (1976); J. C. Clark, G. H. Phillips; M. R. Steer, J. C. S. Perkin I, 475–481 (1976)].

These racemic amino acids are often produced by chemical hydrolysis of CL-5-substituted hydantoins which can be synthesized easily from aldehydes by reaction with potassium cyanide and ammonium carbonate followed by resolution to obtain D(–)-α-amino acids. However, these chemical methods involve complicated steps which are energy intensive, highly polluting and requiring the use of resolving agents.

The species of microorganisms exhibiting hydantoinase activity are Pseudomonas strain IFO 12996; *Pseudomonas putida* DSM 84; *Agrobacterium radiobacter*, NRRL, 11291; *Alkalophilic Bacillus* sp. 123-3 and *Agrobacterium rhizogenes* IFO 13259. These microorganisms shown the potentiality to convert prochiral hydantoins giving chiral D(–)-N-carbamoylaminoacids [Yamada, Hideak; Takahashi, Satomi; Yoneta, Kogi Kanegafuchi Chemical Industry Co. Ltd. Jpn Kokai 78,44690 (1978); U.S. Pat. No. 4,094,741 (1978); CA 89, 74216J, (1919); Degen, Ludwig; Viglia, Aurelio; Fascetti, Eugenio; Perricone, Elene SNAP Progeti Spa; Ger. Offen, 2,631,018 (1977); U.S. Pat. No. 4,111,749 (1978) CA: 86: 167160q (1977); R. Oliveri, F. Fascetti, L. Angelini and L. Degen., Biotech. & Bioeng., 23, 2173–2183 (1981); K. Soda, H. Tanaka, N. Esaki, Amino acids edited H. Dellweg, Biotechnology Vol. 3, 496 (1983), published: Verlag Chemie, Weinhein; S. Takahashi, Progress in Industrial microbiology in Biotechnology of amino acid production, editor H. Yamada et al. Elsevier Publications, Kodansha Ltd. Tokyo, Vol. 24, p. 269 (1986); A. Morin, W. Hummel and M. R. Kula, Applied Microbiology & Biotechnology, 25, 91–96 (1986); H, Yamada, S. Shimizu, H. Shimada, Y. Tani, S. Takashi, T. Ohashi, Biochemie, 62, 395–399 (1980), CA: 93, 68652 (1980); T. Mamoru, H. Takashi, T. Hitoshi, T. Shinichiro, M. Nobuyoshi, Jpn. Kokai 61,212,292 (1986); CA: 106, 100853 (1987); Kanegafuchi Chemical Industry, Jpn. Kokai 81,01,910 (1981), CA: 95, 40842 (1981); J. Kamphuis, W. H. H. Boesten, Q. B. Broxterman, H. F. M. Hermes, J. A. M. Balken, E. M. Plexjer & H. E. Shoemaker; New Developments in chemoenzymatic production of amino acids in Advances in Biochemical Engineering/Biotechnol. Vol. 42, 134–186, edited Aflechter, Publisher Springe-Verlag Berlin, Heidelberg, 1990].

In all heterto known processes a medium for the production of hydantionase consisted of basal mineral salts like $KH_3PO_4$, $MgSO_4$, $MnSO_4$ supplemented with beef extract, Yeast extract or peptone.

The D(–)-N-carbamoylaminoacid can be converted to D(–)-α-amino acid by either chemical method [D. G. Sandro, P. Antonio, R. Luciano, Eur. Pat. 2,88,795 (1988), CA: 110, 193397f (1989); S. Takahashi; T. Ohashi, Y. Kii, H. Kumagai and H. Yamada, J. Ferment. Technol., 57, 328–332 (1979); O. Takehissa; F. Hirotaka, T. Satomi, N. Kenji, Jpn. Pat. 78,10,441 (1978), CA: 90, 39270 (1979)] or by enzymatic methods using N-carbamoylaminoacid amidohydrolase [T. Mamoru, T. Shinichiro H. G. Takashi, T. Hitoshi, Jpn. Kokai 61,177,992 (1986), CA: 106, 17041u (1987); R. Olivieri, E. Fascetti, L. Angelini, L. Degen, Enzyme microbial Technol., 1, 201–204 (1979), CA: 91, 170502 (1979)] from *Agrobacterium radiobacter*, Arthrobacterium and Pseudomonas sps.

The prior art processes for decarbamoylation involve the use of the enzyme (N-carbamoylaminoacid amido hydrolase) which is not readily available, while the chemical process involve the reaction of sodium nitrite in the presence of mineral acid or cation resin, where the product concentration is very low i.e. 1.5 to 2.5%. Concentration of aqueous solution in order to isolate the product from the reaction mixture is required which is energy-intensive process.

As compared to known process, the inventors by their R&D work developed an easier process for D(–) phenylglycine via D(–)-N-carbamoylphenylglycine from DL-5-phenylhydantoin using bacterial cells as the biocatalyst. The strain Pseudomonas sp NCIM 5070 (ATCC 55940) used in these studies could grow well in the medium derived from cheap carbon sources like molasses and was able to produce 3–4% D(–)-N-carbamoylphenylglycine from DL-5-phenylhydantoin within 6 hrs and its decarbamoylation with sodium nitrite in presence of mineral acid of appropriate strength. The strain used the present invention, Pseudomonas sp., was deposited under the Budapest Treaty with the American Type Culture Collection (ATCC), now located at 10801 University Boulevard, Manassas, Va. 20110-2209, on Mar. 11, 1997, under accession No. ATTC 55940, as well as with the National Collection of Industrial microorganisms (NCIM), National Chemical Laboratory (NCL), Pune 411008, India, under accession No. NCIM 5070.

The yield of the product in the invented process is 85–90% in each step and process involves the use of basic chemicals such as CL-5-phenylhydantoin, molasses, sodium nitrite, mineral acid (sulphuric acid, hydrochloric acid) and D(–)-N-carbamoylphenylglycine.

The main objective of the present invention is to develop a improved process for the production of D(–)-phenylglycine from DL-5-phenylhyantion using D-hydantoinase.

Accordingly, this invention provides an improved and easier process for the production of D(–)-phenylglycine via D(–)-N-carbamoylphenylglycine from DL-5-phenylhydantoin.

Salient features of the invention viz., the preparation of hydantoinase enzyme by growing the strain NCIM5070 (ATCC55940) in molasses and used for the conversion of DL-5-phenylhydantoin to D(–)N-carbamoylphenylglycine and its decarbamoylation is carried out with sodium nitrite in the optimized strength of sulphuric acid, where the product concentration is 7 to 10%, avoiding the concentration process of aqueous solution in order to isolate the product from reaction mixture. The product is isolated according to the process of this invention by adjusting the pH of the reaction mixture with sodium hydroxide/ammonium hydroxide.

The Pseudomonas strains available with use were screened along with a few isolates for the production of D(–)-N-carbamoylphenylglycine from DL-5- phenylhydantoin. Though 10 cultures showed hydantoinase activity to obtain D(−)-N-carbamoylphenylglycine from 5-phenylhydantoin, one of them exhibited higher hydantoinase activity after growing in molasses medium. Therefore, further studies on optimization of D(−)-N-carbamoylphenylglycine production were carried out using this strain of Pseudomonas sp. (NCIM 5070) (ATCC 55940). The culture gave high yields of D(−)-N-carbamoylphenylglycine (isolated yield 89%) as a solution of 3–4% strength. The conversion achieved is 89–92%. The train was catalase positive with optimum growth temperature between 25–28° G=C contains of the DNA is 66–67 moles % (buoyant density). The denitrification does not occur.

The Pseudomonas cultures were individually grown in nutrient broth medium and the cells after centrifugation were used for the production of D(−)-N-carbamoylphenylglycine from DL-5-phenylhydantoin. The cultures giving good conversion (>75%) within short period (4 hrs) were further screened for their growth on molasses medium. Only one culture Pseudomonas sp. NCIM 5070 (ATCC 55940) exhibited better hydantoinase activity after growth in molasses medium. The optimization studies carried out using this strain showed that a temperature between 25–35° C. & pH range between 8.0–9.5 were more suitable for D(−)-N-carbamoylphenylglycine. Thus, D(−)-N-carbamoylphenylglycine was obtained within 4–6 hrs using alkaline buffer systems in 10 liter fermenter with a product concentration f 3–4%, which is further chemically converted to D(−)-phenylglycine.

EXAMPLE 1

Nearly 100 bacterial cultures were screened for conversion of DL-5-phenylhydantoin to D(−)-N-carbamoylphenylglycine. Pregrown culture (7 ml) in nutrient broth (beef extract 1%, NaCl 0.5%, peptone 1.0%, pH 7.2) was inoculated into 250 ml conical flask containing 70 ml nutrient broth. The flask was incubated for 10–24 hrs at 30° C. on a rotary shaker. Cells after centrifugation were suspended in 30 ml bicarbonate buffer of pH 8.0–10.0 containing hydantoin (100 mg). The transformation of DL-5-phenylhydantoin was carried out at 30° C. for 4 hrs & 6 hrs. The D(−)-N-carbamoylphenylglycine produced was estimated by p-dimethylamino benzaldehyde reagent (PDAB). Ten cultures showed better conversion of hydantoin to D(−)-N-carbamoylphenylglycine (>75%), which are mentioned in Table 1.

TABLE 1

Hydantoin-hydrolyzing activity of selected strains with 0.33% substrate concentration.

| Strain | Others No | NCIM No. | Conversion (%) 4 h | 6 h |
|---|---|---|---|---|
| Ps. aureofaciens | ATCC 13985 | 2026 | 85.40 | 91.40 |
| Ps. fluorescens | IFO 3081 | 2100 | 76.80 | 89.50 |
| Ps. desmolyticum | NCIB 9427 | 2112 | 100.00 | 100.00 |
| Ps. fluorescens | ATCC 12633 | 2141 | 83.90 | 89.50 |
| Ps. acidovorans | ATCC 15668 | 2861 | 73.50 | 100.00 |
| Ps. aeruginosa | ATCC 15442 | 2862 | 98.50 | 100.00 |
| Ps. pseudoalcaligenes | ATCC 17740 | 2864 | 100.00 | 100.00 |
| Ps. oleovorans | ATCC 8062 | 2867 | 100.00 | 100.00 |
| Ps. Species | NCL isoalate | 2875 | 81.00 | 96.20 |
| Ps. Species | ATCC 55940 | 5070 | 100.00 | 100.00 |

EXAMPLE 2

The strains selected in example 1 were further screened for their growth in cheaper media like molasses with retention of hydantoinase activity. The strain, Pseudomonas sp. NCIM 5070 (ATCC 55940) exhibited high hydantoinase activity after growth in molasses medium (1% molasses) compared to other strains, which are shown in Table 2. This strain was further used for optimization studies on D(−)-N-carbamoylphenylglycine production in both shake flask and ten-liter fermenter.

TABLE 2

The hydantoin hydrolysing activity of selected Pseudomonas strains grown in medium containing only 1% molasses.

| Strain | NCIM No. | Biomass (mg dry weight) | Conversion (%) 4 h | 24 h |
|---|---|---|---|---|
| Ps. aureofaciens | 2026 | 140 | 28.9 | 35.72 |
| Ps. fluorescens | 2100 | 80 | 38.5 | 55.60 |
| Ps. desmolyticum | 2112 | 54 | 55.12 | 76.50 |
| Ps. fluorescens | 2141 | 46 | 37.38 | 69.50 |
| Ps. acidovorans | 2861 | 60 | 28.38 | 62.80 |
| Ps. aeruginosa | 2862 | 47 | 47.00 | 72.00 |
| Ps. pseudoalcaligenes | 2864 | 41 | 37.00 | 39.00 |
| Ps. oleovorans | 2867 | 45 | 52.60 | 78.00 |
| Ps. Species | 2875 | 42 | 37.00 | 52.20 |
| Ps. Species | 55940 | 65 | 70.25 | 87.00 |

EXAMPLE 3

The culture, Pseudomonas sp. NCIM 5070 (ATCC 55940) was grown in molasses medium (1%) for 10–24 hrs at 30° C. The cells were harvested by centrifugation and used for the production of D(−)-N-carbamoylphenylglycine using different buffer systems like phosphate (7–8 pH), borate (8–9 pH), borax-sodium hydroxide (8–10 pH), bicarbonate (8–10 pH) or tris buffer (8–10 pH) and at different temperatures varying from 25° to 35° C. The optimization studies revealed that maximum conversion (>95%) of DL-5-phenylhydantoin to D(−)-N-carbamoylphenylglycine was obtained at alkaline pH (8–9.5) and at ambient temperature $30\pm1°$ C.

EXAMPLE 4

Under the optimized conditions mentioned in example 3; the transformation of DL-5-phenylhydantoin to D(−)-N-carbamoylphenylglycine was carried out in ten liter fermenter. The culture (NCIM 5070) (ATCC 55940) was grown in the New Brunswick (NBS) 14 L capacity fermenter with 10 L working volume of medium containing 4.5% molasses and 2.0% CSL respectively. After sterilization fermenter was inoculated with 1 L of pregrown culture in molasses medium for 24 h at 30° C. Temperature of the fermenter was maintained at 29+1° C. and air flow at 5 L/h (0.5 vvm). Stirrer speed was varied between 400–600 rpm for maintaining the dissolved oxygen (D.O.) at 20% saturation throughout the growth period. Foam was controlled by the addition of sterile silicon antifoam agent. Cells in the fermenter were harvested after 21 h by centrifugation in continuous sharple centrifuge (feed rate 10 L/h). Total biomas obtained from 30 L molasses was 620 parts (wet weight) which was corresponding to 150 parts of dry weight.

The reaction was carried out in 10 L (working volume) 0.05M bicarbonate buffer, pH 9.3 containing 315 parts (wet weight) whole cells and 315 parts (1.73 mole parts) of DL-5-phenylhydantoin. The reaction was carried out at 30° C. with stirring speed of 700 rpm. The pH of the reaction mixture was maintained at 8.5 pH by automatic addition of 3.3N KOH. The product formation with time was correlated to the alkali addition and confirmed by analysing the N-carbamoylphenylglycine by PDAB method. The reaction was completed in 6 hrs giving >90% of D(-)N-carbamoylphenylglycine. The reaction mixture was centrifuged and the broth was separated from the cell mass.

EXAMPLE 5

The D(-)-N-carbamoylphenylglycine produced in example 4 was precipitated from the broth at acidic pH using trichloroacetic acid, hydrochloric acid or sulphuric acid and separated by filtration. The product D(-)-N-carbomoylphenylglycine 310 parts (1.59 mole parts, 89.2%) was obtained having rotation $(\alpha)^r = -157°$, c=0.2 in ethanol [155°, c=0.22 in ethanol, K. H. Dudley and D. L. Bius, J. Heterocyclic Chem., 10, 173–180 (1973)].

EXAMPLE 6

D(-)-N-Carbamoylphenylglycine 2 parts (10.1 mmole parts) was mixed with 1N sulphuric acid 400 parts and cooled to 15° C. A solution of sodium nitrite 1 part (14.5 mmole parts) was added dropwise in 60 minutes. After addition of sodium nitrite solution the reaction mixture was stirred for one hour and analysed by HPLC, showed 93% product. The product was precipitated by adjusting pH 6 with ammoniumhydroxide and the solid was separated by filtration (5.2 mmole parts, 52% yield).

EXAMPLE 7

D(-)-N-Carbamoylphenylglycine 2 parts (10.1 mmole parts) was mixed with 2N sulphuric acid 200 parts and cooled to 15° C. A solution of sodium nitrite 1 part (14.5 mmole parts) was added dropwise in 60 minutes. After addition of sodium nitrite solution the reaction mixture was stirred for one hour and analysed by HPLC, showed 92.5% product. The product was precipitated by adjusting pH 6 with ammonium hydroxide and the solid was separated by filtration (5.6 mmole parts, 56% yield).

EXAMPLE 8

D(-)-N-Carbamoylphenylglycine 2 parts (10.1 mmole parts) was mixed with 4N sulphuric acid 100 parts and cooled to 15° C. A solution of sodium nitrite 1 part (14.5 mmole parts) was added dropwise in 60 minutes. After addition of sodium nitrite solution the reaction mixture was stirred for one hour and analysed by HPLC, showed 93.5% product. The product was precipitated by adjusting pH 6 with ammonium hydroxide and the solid was separated by filtration (6.56 mmole parts, 65% yield).

EXAMPLE 9

D(-)-N-Carbamoylphenylglycine 132 parts (680.0 mmole parts) and was added in 4 equal portion to a four necked flask equipped with mechanical stirrer containing 4N sulphuric acid 600 parts to 15° C. A solution of sodium nitrite 61 parts (884.0 mmole parts) was added dropwise in 6 hours. After complete addition of sodium nitrite solution the reaction mixture was stirred for one hour and analysed by HPLC, showed 94.7% product. The product was precipitated by adjusting pH 6 with ammonium hydroxide and the solid was separated by filtration (605.9 mmole parts, 87.8% yield), HPLC purity and optical purity of the isolated product are 99% and 99.7% respectively, $\{[\alpha]=-157.8°\}$.

Characteristics of the strain:

The strain is gram negative, nonporulating small rods with optimum growth temperature between 25–28° C. The strain is catalase positive. To our knowledge, it appears to be Pseudomonas sp. according to morphological & physiological characteristics. Its G+C content of DNA is 66–67 mole percent.

Advantages of the present process:

The applicants have isolated the Pseudomonas strain which is capable of growing in cheaper substrates like molasses and corn steep liquor and converting Dl-5-phenylhydantoin at faster rate to D(-)N-carbamoylphenylglycine. Yielding high concentration of the product (3–3.5%) which is not reported till today (Examples 1–4).

The development of a method for easy isolation of D(-)N-carbamoylphenylglycine with 90% recovery from the reaction broth (Example 5).

The development of a chemical process for the decarbamoylation of D(-)N-carbamoylphenylglycine to C(-) phenylglycine in 87.8% yield having 99.7% optical purity which can be easily separated by mere pH adjustment of reaction mixture (without concentration of reaction mixture) which has not been reported so far (Example 6–9).

The present process is superior to the reported ones as the product concentration of the reaction mixture is more than 10% which results in easier isolation of the product by mere pH adjustment.

We claim:

1. A microbial process for the preparation of D(-)-N-carbamoylphenylglycine from DL-5-phenylhydantoin which comprises culturing the strain Pseudomonas sp. having Accession No. and deposited with the American Type Culture Collection (ATCC), Manassas, Va., having a hydantoinase activity, in a medium for 16–20 hrs, the medium containing a supplement selected from the group consisting of 1–45% of molasses and 2% cornsteep liquor, separating the cells by centrifugation, treating the solid cells obtained with DL-5-phenylhydantoin in buffer at a pH range of 8–9.5, at a temperature in the range of 25–30° C. for a period of 2–6 hrs, acidifying the mixture to obtain solid D(-)-N-carbamoylphenylglycine and separating the product by filtration.

2. A process as claimed in claim 1, wherein the acid used for acidifying the mixture is selected from the group consisting of trichloroacetic acid, hydrochloric acid, and sulphuric acid having a concentration of 5 to 10N.

* * * * *